United States Patent [19]

Horton et al.

[11] Patent Number: 4,975,937

[45] Date of Patent: Dec. 4, 1990

[54] HEAD ACTIVATED FLUOROSCOPIC CONTROL

[76] Inventors: Jerry L. Horton, Rt. 2 P.O. Box 20460, Benton, La. 71006; Claude H. Baines, 8308 Creekdale St., Shreveport, La. 71107

[21] Appl. No.: 498,634

[22] Filed: Mar. 26, 1990

[51] Int. Cl.$^5$ .................. H05G 1/56; H05G 1/54; G01J 5/10; G01J 1/36

[52] U.S. Cl. .................... 378/114; 378/117; 378/113; 250/338.1; 250/342

[58] Field of Search .............. 378/114, 117, 99, 210, 378/110, 108, 115; 334/8, 13, 16, 17, 29, 47, 89; 250/338.1, 340, 341, 342, 345; 455/603

[56] References Cited

U.S. PATENT DOCUMENTS

| | | | |
|---|---|---|---|
| 3,986,030 | 10/1976 | Teltscher | 250/349 |
| 4,040,744 | 8/1977 | Schertz et al. | 250/342 |
| 4,091,273 | 5/1978 | Fuller et al. | 455/603 |
| 4,156,134 | 5/1979 | Minner | 455/603 |
| 4,377,006 | 3/1983 | Collins et al. | 455/603 |
| 4,673,911 | 6/1987 | Yoshida | 187/100 |
| 4,844,493 | 7/1989 | Kramer | 250/342 |

Primary Examiner—Janice A. Howell
Assistant Examiner—Don Wong
Attorney, Agent, or Firm—John M. Harrison

[57] ABSTRACT

A head-activated fluoroscopic control which is characterized in a preferred embodiment by a continuous wave infrared transmitter located in a cartridge adapted for attachment to eyeglasses, a headband or other headpiece worn by a surgeon or attending physician and a detector or receiver tuned to the frequency of the continuous wave infrared transmitter for receiving a partially collimated infrared signal beam and activating a fluoroscope. The infrared transmitter emits the collimated beam and the beam is received by the receiver when the surgeon's head is turned toward the fluoroscope monitor upon which the receiver rests or in which the receiver is mounted, to facilitate selective operation of the fluoroscope during surgery.

20 Claims, 2 Drawing Sheets

HEAD ACTIVATED FLUOROSCOPIC CONTROL

BACKGROUND OF THE INVENTION

1. Field of the Invention

This invention relates to operation of x-ray fluoroscope devices during surgery and more particularly, to a head-activated fluoroscopic control which includes a transmitter for transmitting partially collimated, continuous wave electro-magnetic radiation such as infrared radiation, and a receiver for receiving the electromagnetic radiation. The transmitter is located in a small cartridge adapted for mounting on the eyeglasses, headband or alternative headpiece of a surgeon or assisting physician and the receiver includes an electromagnetic detection circuit combined with a phase-lock type frequency detector which is tuned to the frequency of the electromagnetic radiation emitted by the transmitter. The receiver may be either located in close proximity to a fluoroscope monitor, or built into the monitor, while the fluoroscope is typically characterized by a C-arm unit having an x-ray tube and beam collimator positioned above the operating table and an image intensification unit located beneath the operating table to facilitate operation of the fluoroscope responsive to turning of the surgeon or attending physician's head toward the fluoroscope monitor and transmission of the electromagnetic radiation in a partially collimated beam from the transmitter to the receiver.

The use of fluoroscopic radiation is widespread in many surgical procedures, as well as diagnostic testing performed in medical centers around the world. Activation of the fluoroscopic x-ray energy is traditionally initiated by a surgeon or attending physician using a foot-operated switch. Because the foot-operated switch is located on the floor beneath the operating table where it cannot be easily viewed by the surgical team, it may be accidentally activated by one or more members of the team during the surgical procedure. Furthermore conductive body fluids may be spilled on the foot switch during the procedure, thereby causing it to malfunction. Moreover, it may be difficult for some physicians to operate the foot switch due to personal handicaps and the foot switch may be easily accidentally activated for an excessive period of time due to distractions in the operating room. The activation of fluoroscopic x-ray energy due to any one of the above circumstances results in useless, unnecessary and sometimes dangerous ionizing exposure to the patient. From observations of fluoroscopic procedures, it has been observed that up to 10% of the fluoroscopic x-ray time used during an average surgical procedure is non-productive. In practice, any needless x-ray exposure to patients or hospital workers should be avoided since the ionizing effect of x-rays to the body are cumulative. Accordingly the head-activated fluoroscopic control of this invention facilitates a highly satisfactory technique for using fluoroscopic radiation on demand in an optimum manner by the surgeon or attending physician without needless x-ray exposure to the patient and without the necessity of using the hands or feet of the surgeon or attending physician.

Upon analyzing the problem of more efficient use of fluoroscopic radiation in surgical procedures, it was noted that the physicians or surgeons do not need fluoroscopic x-ray until their eyes are focused on the fluoroscopic x-ray monitor. A continuous wave, compact infrared source cartridge was devised which is sufficiently small and light to be clipped or otherwise attached to eyeglasses, a headband or an alternative headpiece. A highly sensitive infrared detection circuit, combined with a phase-lock type frequency detector tuned to the frequency of the transmitter, was also developed as a receiver to detect the partially collimated infrared beam emitted by the transmitter cartridge. Using a combination of source beam and detector collimation and by adjusting the overall system sensitivity, an optimum triggering zone was created which allows accurate activation of the fluoroscopic x-ray, thus minimizing the unintentional fluoroscopic radiation which a patient often receives during surgery. The device also eliminates the necessity for using an awkward foot switch located on the floor beneath the operating table. The receiver is mounted on or in close proximity to the fluoroscopic x-ray monitor, which faces the area where the assisting or attending physician or surgeon normally stands during an operating room procedure and the relay contacts of the receiver are attached in parallel to the normal fluoroscopic x-ray foot switch contacts. During a typical fluoroscopic x-ray procedure, whenever the physician turns his head toward the monitor, a partially collimated, cone-shaped transmitter beam continuously emitted from the transmitter cartridge strikes the receiver and the fluoroscopic x-ray device is activated as if the conventional foot switch had been pressed. The beam collimation adjustment in the transmitter is such that the physician's line of sight must be directly at the fluoroscopic x-ray monitor to activate the receiver and energize the fluoroscope device. Conversely, when the physician turns his head away from the monitor the beam no longer strikes the receiver and operation of the fluoroscope device is terminated.

2. Description of the Prior Art

Various types of remote control switching systems are known in the art. An electro-optical switching system is detailed in U.S. Pat. No. 4,091,273, dated May 23, 1978, to William D. Fuller, et al. The system includes multiple visually activated switches, one for each one of a plurality of different electronic apparatus, each including electromagnetic radiation sensors having a detection surface and each controlling the application of electrical powe to the respective equipment in response to an impinging electromagnetic beam incident at the detection surface for a determined time interval. A pulsed electromagnetic beam is provided by a transmitter included within an electrical magnetic activating source which is held or disposed on a portion of the anatomy of the human operator who aligns the beam with the detection surface on the selected one of the switches with the aid of a visual reticle image provided by a reticle generator included in the activating source and boresighted with the transmitter. The system further includes control unit responsive to each of the radiation sensors for discriminating between the pulsed electromagnetic beam energy and the ambient energy background and for providing actuating signals to the respective equipment in response to the presence of incident pulsed electromagnetic energy at the associated visually activated switch detection surface for a determined time interval in the absence of incident pulsed electromagnetic energy at each of the other switches within the same time interval, the control unit providing actuation of the various selected equipment sequentially, one at a time. A "Remote Control Device for Operation by Radiation" is detailed in U.S. Pat. No.

4,156,134, dated May 22, 1979, to Willy Minner. The device operates by means of radiation and includes a receiver for the radiation and means for transforming the radiation into an electric signal, as well as rectification means for rectifying an electric signal. U.S. Pat. No. 4,377,006, dated Mar. 15, 1983, to Johnny Collins, et al, details an "IR Remote Control System". The remote control system is designed for a television receiver and includes a transmitter and a receiver, the transmitter being adapted for transmitting a multibit code identifying a selected function of the television receiver, wherein the data bits forming the multibit code each include a single pulse representing a first logic state and a grouping of at least two relatively close spaced pulses representing second logic state. The remote control receiver includes a self-locking detector for converting the transmitted pulses to a binary logic signal and decoding apparatus responsive to the logic signal for operating the selected television receiver function. U.S. Pat. No. 3,475,092, dated Oct. 28, 1969, to D. M. Harvey, details a "Wireless Remote Control Slide Changer". The device is designed for selectively actuating forward and reverse changing mechanism of a projector such as slide projector. The system includes a hand-held control unit which develops a pulse length modulated beam of actinic radiation for energizing photosensitive receiver mounted on the slide projector. The beam of light is chopped by using an alternatively opaque and transparent rotating or vibrating grate. An elevator remote-control apparatus is detailed in U.S. Pat. No. 4,673,911, dated June 16, 1987, to K. Yoshida. The remote control apparatus is designed such that when a desired call has been registered with the "up" button or "down" button of a remote controller an acceptance signal is delivered from an elevator control device to turn the "up" button or "down" button of the hall button device on. At the same time, a response signal corresponding to the acceptance signal is sent from the transmitter of the hall button device to the remote controller and it is received by the receiver of the remote controller, to activate the response lamp in correspondence with the call registration. Accordingly, the ascent or descent registration of an elevator can be reliably acknowledged on the remote controller side.

It is an object of this invention to provide a head-activated fluoroscopic x-ray control system which eliminates the requirement of a conventional foot switch in operating a fluoroscopic x-ray and monitor.

Another object of the invention is to provide a head-activated fluoroscopic control which is characterized by a partially collimated beam source for transmitting continuous wave electromagnetic radiation and a receiver device to detect the radiation beam and actuate set of relay contacts to selectively operate a fluoroscopic x-ray and monitor.

Yet another object of this invention is to provide head actuated control system for operating a fluoroscope during operating room procedures, which system includes a head-mounted transmitter cartridge capable of emitting a continuous cone-shaped beam of infrared radiation and a infrared receiver mounted in or located in close proximity to a fluoroscope monitor for receiving the beam and activating the fluoroscope.

Still another object of the invention is to provide a head activated control system for a fluoroscope, and a C-arm fluoroscope in particular, which control system includes an infrared emitter cartridge capable of emitting a continuous, partially collimated, cone-shaped beam of infrared radiation and a receiver built into or resting on the fluoroscope monitor, which receiver is provided with an infrared detection circuit for receiving the infrared radiation and triggering operation of the fluoroscope responsive to moving the head and viewing the monitor.

A still further object of this invention is to provide an infrared transmitter adapted for mounting on the eyeglasses, headband or alternative headpiece of a surgeon or attending physician, for emitting a continuous partially collimated infrared beam and an infrared receiver positioned in close proximity to a fluoroscopic x-ray monitor for receiving the collimated infrared beam and activating a fluoroscopic x-ray device located over an operating table.

Another object of the invention is to provide a head-activated fluoroscopic control which includes a cartridge transmitter capable of transmitting a continuous wave source of partially collimated infrared radiation and provided with a light weight cable, which transmitter can be adapted to mount on a headband, goggles, eyeglasses or an alternative headpiece and further including a highly sensitive infrared detector mounted on, in or near a fluoroscopic x-ray monitor, wherein the collimated beam emitted by the transmitter is received by the receiver responsive to turning of the surgeon's or physician's head toward the monitor, in order to activate the fluoroscopic x-ray and monitor.

SUMMARY OF THE INVENTION

These and other objects of the invention are provided in a new and improved head-activated fluoroscopic control which is characterized by an infrared transmitter capable of emitting a continuous, partially collimated, cone-shaped wave source of infrared radiation for a selected distance, a sensitive infrared detector located on or mounted in a fluoroscopic x-ray monitor facing the operating area, wherein the receiver receives the carefully collimated beam of infrared radiation and activates the fluoroscopic x-ray and monitor responsive to turning of the physician's or surgeon's head toward the monitor.

BRIEF DESCRIPTION OF THE DRAWING

The invention will be better understood by reference to the accompanying drawings wherein.

DESCRIPTION OF THE PREFERRED EMBODIMENTS

Figure 1:
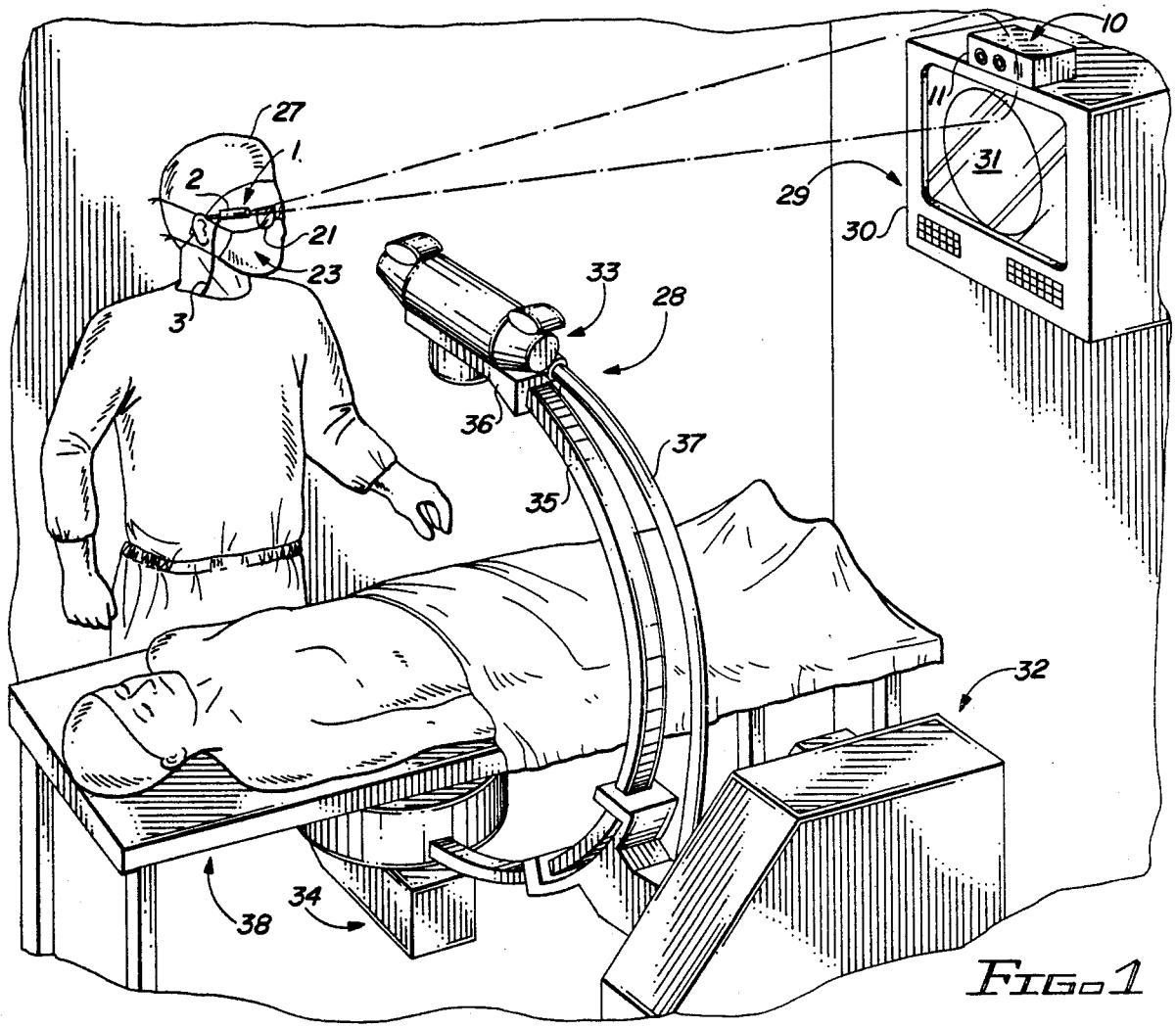
FIG. 1 is a perspective view of a physician, an operating table and a patient lying on the operating table, along with transmitter and receiver elements of a preferred embodiment of the head-activated fluoroscopic control of this invention.
Figure 2:
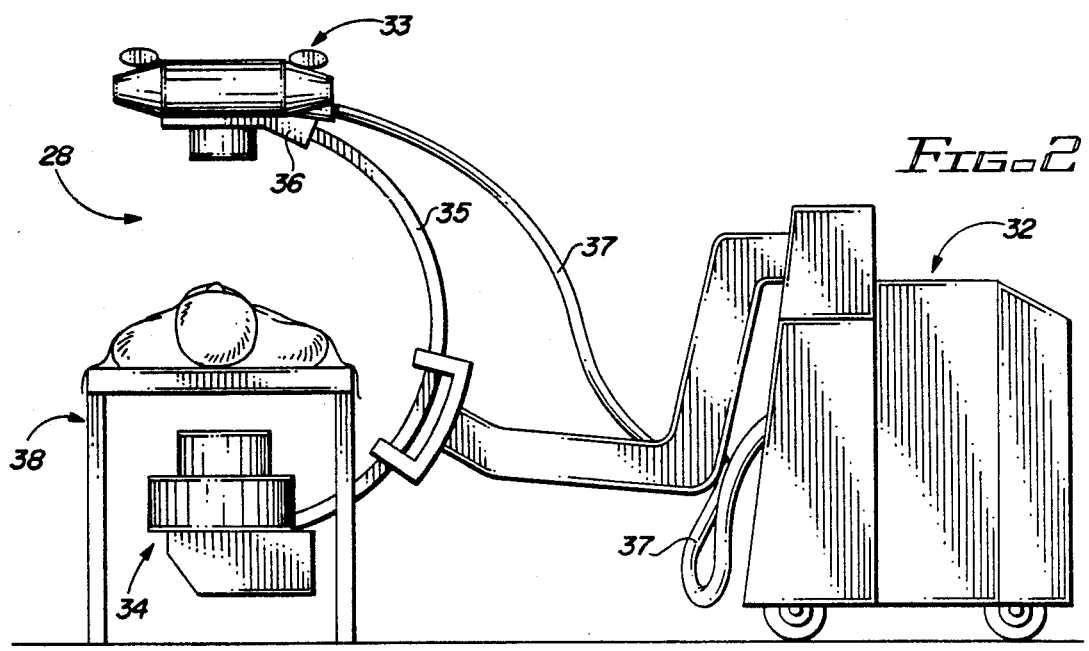
FIG. 2 is a side view of the physician, operating table, patient and head actuated fluoroscope control elements illustrated in FIG. 1.
Figure 3:
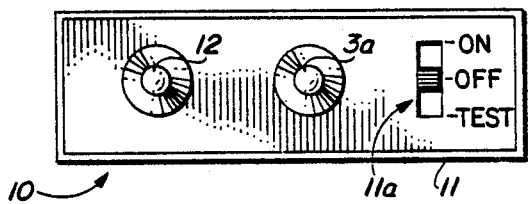
FIG. 3 is a front view of a typical infrared receiver for placement on the fluoroscope monitor of a fluoroscopic x-ray device.

Referring to FIGS. 1–3 of the drawings, the head activated fluoroscopic control of this invention includes an infrared source or transmitter 1, mounted on the earpiece of eyeglasses 21, worn by the physician, and an infrared receiver 10, resting on a fluoroscope monitor 29. A C-arm fluoroscope 28 includes an x-ray tube and beam collimator 33, complete with control wiring 37, mounted on a mount bracket 36 and positioned directly over a patient reclining on an operating table 38. The mount bracket 36 is mounted in adjustable, sliding relationship on a curved C-arm 35, which extends from the mount bracket 36 to an image intensification unit 34, located beneath the operating table 39. The fluoroscope 28 is designed to selectively x-ray the patient by operation of the head-activated fluoroscopic control of this invention, and display the x-ray picture on the fluoroscope monitor 29, as hereinafter further described. As further illustrated in FIG. 1, the fluoroscope monitor 29 includes a monitor cabinet 30, having a round cabinet screen 31, for viewing by the attending physician. The infrared receiver 10 is further characterized by a receiver housing 11, having a sensor window 12 for receiving the cone-shaped infrared radiation beam 9, emitted from an emitter cartridge 2, provided with cartridge wiring 3a, which emitter cartridge 2 characterizes the infrared transmitter 1. Accordingly, when the infrared radiation beam 9 strikes the sensor window 12 of the infrared receiver 10 as the physician's head turns toward the fluoroscope monitor 29, the fluoroscope 28 is activated to x-ray the patient 38 and the x-ray picture is displayed on the cabinet screen 31 of the fluoroscope monitor 29. As illustrated in FIG. 3, in a first preferred embodiment of the invention the receiver housing 11 includes the sensor window 12, a test light 3a and a 3-position switch 11a. The three-position switch 11a is placed in the "on" position to arm the infrared receiver 10 and may be manipulated into the "test" position to test the head operated fluoroscopic control without activating the fluoroscope 28. The unit is rendered inoperative by placing the 3-position switch in the middle, or "off" position.

Figure 5:
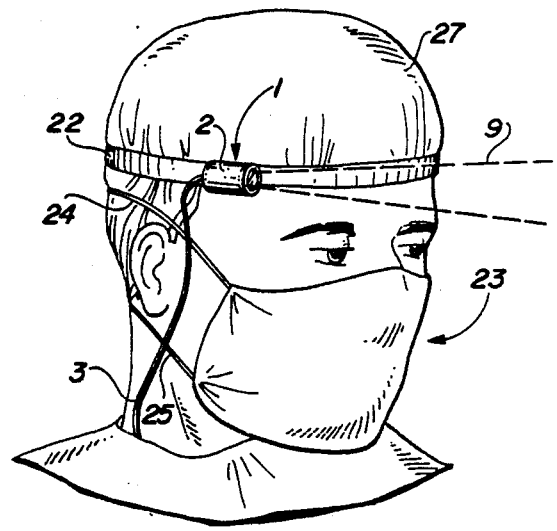
FIG. 5 is a perspective view of a typical infrared emitter cartridge mounted on the headband worn by a physician.
Figure 6:
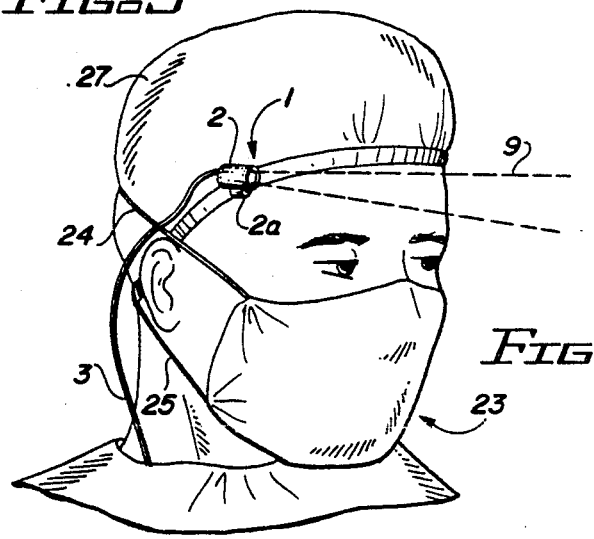
FIG. 6 is a perspective view of the infrared emitter cartridge clipped on a physicians cap.
Figure 7:
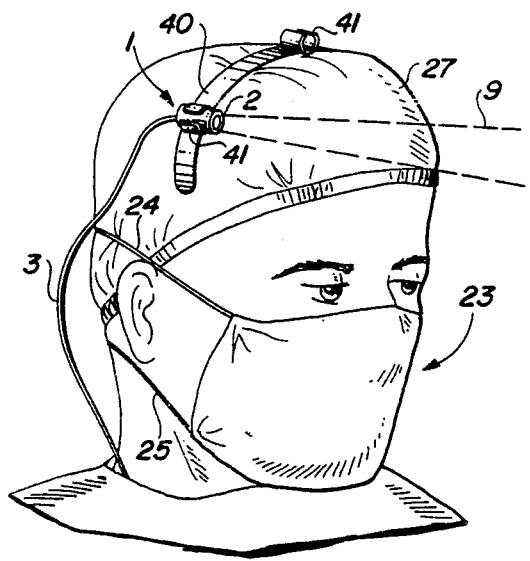
FIG. 7 is a perspective view of the infrared emitter mounted on a head clip.
Figure 8:
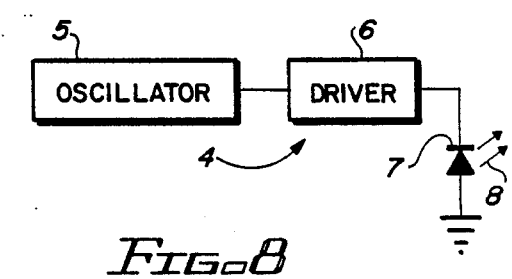
FIG. 8 is a schematic diagram of a typical transmitter circuit.
Figure 9:
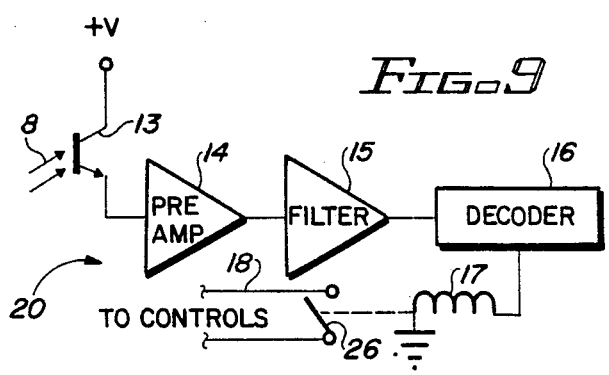
FIG. 9 is a schematic diagram of a typical receiver circuit.

Referring now to FIGS. 5–7 of the drawings, in alternative preferred embodiments of the invention the emitter cartridge 2 of the infrared transmitter 1 can be removably attached by means of a cartridge clip 2a to the headband 22 (FIG. 5) or the head cover 27 (FIG. 6), under circumstances where the physician does not wear eyeglasses. Furthermore, referring to FIG. 7, in another alternative preferred embodiment of the invention the emitter cartridge 2 can be inserted into one of several band clamps 41, spaced on the cartridge band 40, for the same purpose.

Referring now to FIGS. 1, 2, 8 and 9 of the drawings, a typical control cabinet 32 and cooperating circuits for operating the fluoroscope 28, as well as the infrared transmitter 1 and infrared receiver 10 are illustrated. The transmitter circuit 4 illustrated in FIG. 8 includes an oscillator 5, electrically connected to a driver 6, which drives an infrared light-emitting diode 7, to produce infrared radiation 8. Similarly, the receiver circuit 20 illustrated in FIG. 9 includes a sensor 13, which receives and senses the infrared radiation 8, a pre-amplifier 14, electrically connected to the sensor 13, a filter 15 electrically connected to the pre-amplifier 14 and a decoder 16 electrically connected to the filter 15 and to a relay 17. The relay 17 energizes the fluoroscopic x-ray function in the fluoro circuit 18, located in the control cabinet 32 of the fluoroscope 28. The fluoro circuit 18 may also be provided with a foot switch 26 for alternatively manually activating the fluoroscopic x-ray function in conventional fashion.

Figure 4:
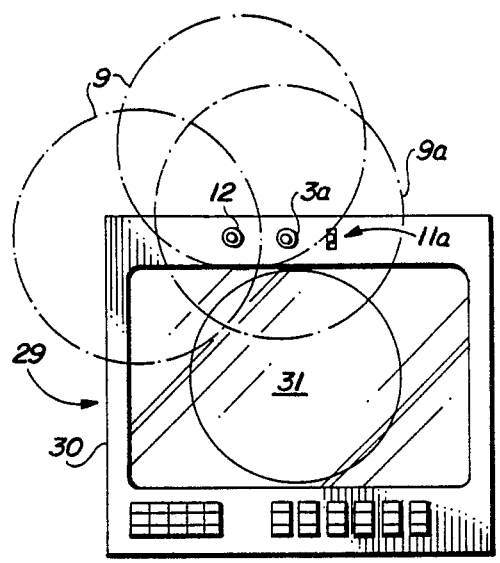
FIG. 4 is a front view of the infrared receiver mounted on the fluoroscope monitor, more particularly illustrating cones of infrared radiation superimposed thereon.

Accordingly, referring again to the drawings, it will be appreciated that the attending physician is free to conduct the planned operating room procedure on the patient without concern as to the location of a conventional foot pedal or other switch device placed on the operating room floor in close proximity to the operating table 38. As illustrated in FIGS. 1 and 4, when it is desired to operate the fluoroscope 28, the physician merely turns his head to face the cabinet screen 31 of the fluoroscope monitor 29 and the infrared radiation beam 9, which is continuously emitted in a controlled collimated cone from the emitter cartridge 2 of the infrared transmitter 1, strikes the sensor window 12 of the infrared receiver 10 in a beam print 9a, illustrated in phantom in FIG. 4. The infrared radiation beam 9 thus activates the sensor 13, pre-amplifier 14, filter 15, decoder 16 and relay 17 of the receiver circuit 20, illustrated in FIG. 9 and operation of the relay 17 causes the fluoroscope 28 to emit x-rays. The results of these x-rays are displayed on the cabinet screen 31 of the fluoroscope monitor 29. Operation of the fluoroscope 28 is immediately terminated when the physician move his head such that he is no longer facing the fluoroscope monitor 29, thus moving the beam print 9a from contact with the sensor window 12 and interrupting contact between the infrared radiation beam 9 and the housing window 12.

Since the infrared transmitter 1 is capable of emitting a continuous, carefully collimated wave source of infrared radiation represented by the infrared radiation beam 9 whether the physician is looking toward the fluoroscope monitor 29 or not, the infrared receiver 10 is almost immediately activated when the physician turns his head to view the fluoroscope monitor 29. However, a slight delay is built into the receiver circuit 20 to facilitate inadvertent turning of the physician's head and scanning the infrared radiation beam 9 across the sensor window 12 without activating the fluoroscope 28. The infrared radiation beam 9 is collimated to an optimum beam angle which yields a beam print 9a of desired area, as illustrated in FIG. 4, which area was determined by trial and error in various fluoroscopic x-ray experiments. Furthermore, the infrared receiver 10 is a highly sensitive infrared detector provided with pre-amplification and filtering functions to operate in all except rapid scanning circumstances of incidence of the infrared radiation beam 9 with the sensor window 12, as further illustrated in FIG. 4. The infrared receiver 10 also operates to reject extraneous pulses which may eminate from other remote control devices, such as video cassette recorders, television sets and the like, as well as ambient noise. A frequency discriminator, (not illustrated) when locked onto the continuous wave source, closes the relay 17, the contacts of which are located in parallel with the fluoro circuit 18. This wiring arrangement does not preclude the use of the foot switch 26, illustrated in FIG. 9, should the head-activated fluoroscopic control device fail for any reason.

It will be appreciated by those skilled in the art that the head-activated fluoroscopic control of this invention allows the physician to concentrate on his work rather than where the foot switch 26 is located at any given time during the operating room procedure. The device can be retrofitted on any existing x-ray machine having fluoroscopic x-ray capability, or the infrared receiver 10 may be built into the fluoroscope monitor 29 component of the device, as illustrated in FIG. 4.

While the preferred embodiments of the invention have been described above, it will be recognized and understood that various modifications may be made therein and the appended claims are intended to cover all such modifications which may fall within the spirit and scope of the invention.

Having described our invention with the particularity set forth above, what is claimed is:

1. A head activated fluoroscopic control for visually operating fluoroscopic x-ray equipment, comprising transmitter means adapted for disposition on the head of an operator and emitting a beam of electromagnetic radiation at a selected frequency substantially along the line of sight of the operator and receiver means spaced from said transmitter means, said receiver means electrically connected to the fluoroscopic x-ray equipment for receiving said beam of electromagnetic radiation responsive to movement of the head of the operator and operating said fluoroscopic x-ray equipment while said beam of electromagnetic radiation is received by said receiver means.

2. The head activated fluoroscopic control of claim 1 wherein said electromagnetic radiation further comprises infrared radiation, said transmitter means further comprises an infrared radiation transmitter and said receiver means further comprises a infrared radiation receiver.

3. The head activated fluoroscopic control of claim 1 wherein said transmitter means further comprises a transmitter attached to an article of headwear worn by the operator.

4. The head activated fluoroscopic control of claim 1 wherein said transmitter means further comprises a transmitter removably attached to an article of headwear worn by the operator, electromagnetic radiation further comprises infrared radiation and said receiver means further comprises an infrared radiation receiver.

5. The head activated fluoroscopic control of claim 3 wherein said headwear further comprises eyeglasses.

6. The head activated fluoroscopic control of claim 3 wherein said headwear further comprises a headband.

7. The head activated fluoroscopic control of claim 1 wherein said beam of electromagnetic radiation is at least partially collimated to define a cone of selected proportions.

8. The head activated fluoroscopic control of claim 4 wherein said infrared radiating is partially collimated to define a cone of selected proportions.

9. A head activated fluoroscopic control for visually operating fluoroscopic x-ray equipment characterized by an x-ray tube and collimation element, an image intensification element and a monitor, said head operated fluoroscopic control comprising transmitter means adapted for removable disposition on the head of an operator and emitting a continuous beam of electromagnetic radiation at a selected frequency substantially along the line of sight of the operator and receiver means spaced from said transmitter means, said receiver means electrically connected to the fluoroscopic x-ray equipment for selectively receiving said continuous beam of electromagnetic radiation responsive to movement of the head of the operator, whereby said fluoroscopic x-ray equipment is operated when the monitor is in said line of sight of the operator and said continuous beam of electromagnetic radiation is received by said receiver means.

10. The head activated fluoroscopic control of claim 9 wherein said transmitter means further comprises an infrared radiation transmitter said electromagnetic radiation further comprises infrared radiation and said receiver means further comprises an infrared radiation receiver.

11. The head activated fluoroscopic control of claim 9 wherein said transmitter means further comprises a continuous wave transmitter attached to an article of headwear worn by the operator.

12. The head activated fluoroscopic control of claim 9 wherein said continuous beam of electromagnetic radiation further comprises a continuous cone-shaped beam of infrared radiation, said transmitter means further comprises a cylindrical transmitter attached to an article Of headwear worn by the operator and said receiver means further comprises an infrared radiation receiver.

13. The head activated fluoroscopic control of claim 12 wherein said headwear further comprises eyeglasses.

14. The head activated fluoroscopic control of claim 12 wherein said headwear further comprises a headband.

15. The head activated fluoroscopic control of claim 9 wherein said continuous beam of electromagnetic radiation is at least partially collimated to define a cone of selected proportions.

16. The head activated fluoroscopic control of claim 15 wherein said transmitter means further comprises an infrared radiation transmitter said electromagnetic radiation further comprises infrared radiation and said receiver means further comprises an infrared radiation receiver.

17. The head activated fluoroscopic control of claim 16 wherein said transmitter means further comprises a continuous wave transmitter removably attached to an article of headwear worn by the operator.

18. A head activated fluoroscopic control for visually operating fluoroscopic x-ray, equipment characterized by an x-ray tube and collimation element, an image intensification element and a monitor, said head operated fluoroscopic control comprising a transmitter removably attached to a headpiece worn by an operator for emitting a continuous cone-shaped beam of infrared radiation substantially along the line of sight of the operator and a receiver spaced from said transmitter, said receiver electrically connected to the fluoroscopic x-ray equipment for receiving said continuous, cone-shaped beam of infrared radiation whereby said fluoroscopic x-ray equipment is operated when the monitor is in said line of sight of the operator and said continuous beam of electromagnetic radiation is received by said receiver.

19. The head activated fluoroscopic control of claim 18 wherein said headwear further comprises eyeglasses.

20. The head activated fluoroscopic control of claim 18 wherein said headwear further comprises a headband.

* * * * *